United States Patent [19]

Davis, III et al.

[11] Patent Number: 4,541,910
[45] Date of Patent: Sep. 17, 1985

[54] METHOD FOR ELECTROBLOTTING MACROMOLECULES FROM A CHROMATOGRAPHIC GEL

[75] Inventors: Fred E. Davis, III, Hamden, Conn.; Johathan M. Gershoni, Rehovot, Israel

[73] Assignee: Yale University, New Haven, Conn.

[21] Appl. No.: 549,474

[22] Filed: Nov. 7, 1983

[51] Int. Cl.[4] .................... G01N 27/26; G01N 27/28
[52] U.S. Cl. ............................. 204/182.8; 204/299 R
[58] Field of Search ............ 204/180 G, 180 R, 299 R

[56] References Cited

U.S. PATENT DOCUMENTS

| 3,255,100 | 6/1966 | Raymond | 204/180 G |
| 3,989,612 | 11/1976 | Kragt et al. | 204/180 G |
| 4,049,534 | 9/1977 | Posner | 204/299 R |
| 4,148,703 | 4/1979 | Trop et al. | 204/180 G |

OTHER PUBLICATIONS

Stellwag, E. et al., "Electrophoretic Transfer of DNA, RNA and Protein onto Diazobenzyloxymethyl (DBM) Paper", *Nucleic Acid Research*, vol. 8, pp. 299–317 (1980).
Tas, J. et al., "A Method for the Quantitative Determination of Protein Incorporated in Solubilizable Polyacrylamide Gels", *Anal. Biochem.*, vol. 100, pp. 264–270 (1982).
Towbin, H. et al., "Electrophoretic Transfer of Proteins from Polyacrylamide Gels to Nitrocellulose Sheets: Procedure and some Applications", *Proc. Nat. Acad. Sci. U.S.A.*, vol. 76, pp. 4350–4354 (1979).
Biorad Laboratories, Manufactures Literature, Jan. 1982.
Gershoni, J. et al., "Protein Blotting: Principles and Applications", *Anal. Biochem.*, vol. 131, pp. 1–15 (1983).
Gibson, W., "Protease-Facilitated Transfer of High--Molecular-Weight Proteins during Electrotransfer to Nitrocellulose", *Anal. Biochem.*, vol. 118, pp. 1–3 (1981).
Howe, J. et al., "A Sensitive Immunoblotting Method for Measuring Protein Synthesis Initiation Factor Levels in Lysates of Escherichia Coli, *J. Biol. Chem.*, vol. 256, 12836–12839 (1981).
McLellan, T. et al., "Serial Electrophoretic Transfers: A Technique for the Identification of Numerous Enzymes from Single Polyacrylamid Gels", *Biochemical Genetics*, vol. 19, pp. 647–654 (1981).
Erickson, P. et al., "Quantitative Electrophoretic Transfer of Polypeptides from SDS Polyacrylamide Gels to Nitrocellulose Sheets: A Method for Their Re-Use in Immunoantoradiographic Detection of Antigens", *J. Immunol. Methods*, vol. 51, pp. 241–249 (1982).
Gershoni, J. et al., "Electrophoretic Transfer of Proteins from Sodium Dodecyl Sulfate-Polyacrylamide Gels to a Positively Charged Membrane Filter", *Anal. Biochem.*, vol. 124, pp. 396–405 (1982).
Arnheim, N. et al., "Heterogeneity of the Ribosomal Genes in Mice and Men" *Cell*, vol. 11, pp. 363–370 (1977).
Bolen, J. et al., "Detection and Quantitation of Newcastle Disease Virus Proteins in Infrared Chicken Embryo Cells", *Appl. Environ. Microbiol.*, vol. 43, pp. 193–199, (1982).
Burnette, W., "'Western Blotting': Electrophoretic Transfer of Proteins from Sodium Dodecyl Sulfate-Polyacrylamide Gels to Unmodified Nitrocellulose and Radiographic Detection with Antibody and Radioiodinated Protein A", *Anal. Biochem.*, vol. 112, pp. 195–203 (1981).
Bittner, Michael et al., "Electrophoretic Transfer of Proteins and Nucleic Acids from Slab Gels to Diazobenzyloxymethyl Cellulose or Nitrocellulose Sheets", *Analytical Biochemistry*, 102 (1980), pp. 459–471.

*Primary Examiner*—Andrew H. Metz
*Assistant Examiner*—B. J. Boggs, Jr.
*Attorney, Agent, or Firm*—Walter J. McMurray

[57] ABSTRACT

An improved method of electroblotting macromolecules from a chromatographic gel is claimed. The method comprises a design for wire electrode arrays that are capable of generating either highly uniform or controlled predetermined gradient electric fields. A gradient electric field is particularly suited for the quantitative electroblotting of proteins with a wide range of molecular weights.

4 Claims, 18 Drawing Figures

METHOD FOR ELECTROBLOTTING MACROMOLECULES FROM A CHROMATOGRAPHIC GEL

BACKGROUND OF THE INVENTION

1. Field of the Invention

This invention relates to macromolecule blotting and more particularly to an improved method for electroeluting and blotting macromolecules from a chromatographic gel to an immobilizing matrix.

2. Prior Art

Smithies, Biochem. J. 61: 629–641 (1955), showed that starch gel could serve as a molecular sieve through which zone electrophoresis of proteins occurs. Since then, there have been constant innovations in the technique of gel electrophoresis. The introduction of acrylamide gels, discontinuous buffer systems, the use of sodium dodecyl sulfate (SDS) to disaggregate protein complexes to be resolved on gels, and the eventual combined use of SDS in discontinuous buffer systems for polyacrylamide gel electrophoresis have been major contributions to the development of one of the most widely used analytical and preparative tools of modern biology.

The main object of these techniques has been to visually demonstrate the homogeneity or complexity of a protein preparation by following the appearance of disappearance of a particular "band" throughout a given experimental procedure. One-dimensional gels were found to be adequate, provided only relatively simple protein samples such as viruses, bacteriophages, erythrocyte ghost membranes, etc., were being analyzed. More complex systems demanded greater resolving power and new two-dimensional gel systems were developed. Today, even the thousands of polypeptides which are a part of the more intricate proteinaceous samples can be efficiently resolved.

The task of unequivocally correlating a "band" or "spot" with a recognized function has often been difficult, and this is even more so when the resolution of the proteins depends on their denaturation. Nevertheless, many approaches have been developed which allow the identification of a specific enzyme, antigen, glycoprotein or hormone receptor, etc., in a gel. These techniques rely on the ability to maintain at least one of the following prerequisites: (1) that the polypeptides retain their activity throughout electrophoresis; (2) renaturation of a denatured polypeptide; and (3) covalent crosslinkage of the protein in question to a detectable ligand prior to electrophoresis. Moreover, the actual processing of the gels entails multiple manipulations and extensive incubations and washing procedures. This is very time consuming and quite often prone to handling accidents such as breakage and tearing of wet gels or cracking during the drying of the gels.

In attempting to overcome some of the problems encountered in analyzing gels, a new approach has evolved. A number of reports have been published demonstrating that the well established approach of "Southern-blotting", i.e., transferring DNA patterns from agarose gels to nitrocellulose membrane filters, can be applied to protein patterns in polyacrylamide gels. Intact protein patterns are eluted from the gels and are immobilized on a filter substratum. The substratum is, in turn, subjected to the same type of procedures which have been used on gels for "band" or "spot" identification. However, by transferring electropheretograms to immobilizing matrices one may benefit from the following advantages: (1) wet filters are pliable and easy to handle; (2) the immobilized proteins are readily and equally accessible to various ligands (since the limitations introduced in gels by differential porosity are obviated); (3) transfer analysis generally calls for small amounts of reagents; (4) processing times (incubations and washings) are significantly reduced; (5) multiple replicas of the gels may be made; (6) transferred patterns may be stored for months prior to their use; (7) protein transfers may undergo multiple analyses. Moreover, the transferred protein patterns are amenable to analyses which would be otherwise extremely difficult or impossible to perform on gels.

The term "blotting" today refers to the process of transferring biological macromolecules such as nucleic acids and proteins from gels to an immobilizing matrix. The term is often used in conjunction with the relevant macromolecule, e.g., protein blotting, DNA blotting and RNA blotting. The resulting filter containing transferred immobilized macromolecule is known as a "blot" or "transfer" and can be incubated with a ligand, a procedure which may be referred to as "overlay". Thus, for example, immuno-overlay, lectin overlay or calmodulin overlay refers to the incubation of a blot with an antibody, lectin or calmodulin, respectively.

In general, protein blotting should be viewed as two sequential events, namely the elution of the polypeptide from the gel and the adsorption of the eluted material to an immobilizing matrix.

Three main driving forces have been exploited for macromolecule elution. One is diffusion. Here, the gel containing the macromolecules to be transferred is sandwiched between two sheets of immobilizing matrix which are in turn sandwiched between foam pads and stainless steel screens. This final assembly is then submerged in two liters of buffer and allowed to sit for 36–48 hours. The result of this incubation is that two identical replica blots are obtained. This may or may not be an advantage. This depends on the quantity of macromolecule present and the sensitivity of the assay to be used. The efficiency of transfer may reach 75% with half the quantity available for each matrix. Since diffusion should occur in all directions loss of resolution might be expected. Because all the macromolecules in the gel are subject to the same diffusive force there is a bias in the speed of elution in favor of the lower molecular weight macromolecules.

This speed bias is a disadvantage especially when the purpose of the technique is to quantify the amount of each component in a particular sample or in comparing samples. The speed bias is also a disadvantage when subdetectable amounts of the higher molecular weight macromolecules are eluted.

The second means of macromolecule blotting is based on mass flow of buffer (convection) through the gel. This is the traditional procedure described by Southern, J. Mol. Biol. 98: 503–517 (1975). The gel is placed in a reservoir of buffer. A membrane filter is applied to the gel and paper towels are piled onto the membrane filter. The towels absorb the buffer from the reservoir through the gel and membrane filter. This movement of fluid serves as the driving force which elutes the proteins out of the gel which are then trapped in the membrane filter to create the blot. The advantages of this technique are that it takes less time (2–12 hrs.) than diffusion blotting, is more efficient, and is inexpensive since a reservoir is the only apparatus required. The major disadvantage is that this method of elution is only practical with agarose gels and is less suitable for use with polyacrylamide gels. A modification of this approach has been suggested which allows bidirectional blotting, i.e., blotting with two membrane filters, one on either side of the gel. The time for efficient solution has been dramatically reduced by applying a vacuum to facilitate the process—Peferoen, et.al., FEBS Lett. 145: 369–372 (1982).

The most widely used mode for protein blotting (it is quite often found to be advantageous in nucleic acid blotting as well) is based on electroeluting the macromolecule from the gel. The concept of electroelution of macromolecules for blotting was originally described by Arnheim and Southern, Cell 11: 363–370 (1977). Subsequently, numerous apparatus designs have been reported and some are commercially available. The essence of the technique is as follows. A wet filter material is placed on a gel making sure that no air bubbles are caught within the filter or between the filter and the gel. The filter and gel are then sandwiched between supportive porous pads such as "Scotch Brite" scouring pads, foam rubber or layers of wet blotting paper. The assembly is then supported by solid grids (usually non-conductive). It is very important that the gel and filter are firmly held together. This ensures good transfer and prevents distortion of the protein bands. The supported "gel+filter sandwich" is inserted into a tank containing "transfer buffer" and placed between two electrodes. The electrodes are connected to a power supply. Typical currents employed are in the range of 250 mA. An economical, yet efficient, design that seems to work reasonably well is that described by Bittner, et.al., Anal. Biochem. 102: 459–471 (1980).

The advantage of electroelution of macromolecules is that the time needed for elution is greatly reduced. Additionally, since the electric field strength used for elution is readily quantifiable and manipulable, the technique is conducive to the determination of exact and readily reproducible optimum transfer conditions.

Several apparatus have been reported which utilized different designs and construction for the electrodes. The design and construction of the electrode system is important because of the need as pointed out by Bittner, et.al., for a uniform electric potential, i.e., a homogeneous field across the entire surface of a chromatographic gel. A homogeneous field is needed to ensure that the macromolecules in the different lanes of the gel are uniformly transferred to the immobilizing matrix. Only then can lane to lane comparisons be made. The ideal way of designing an apparatus which would exert a homogeneous field on a chromatographic gel would be to use two parallel metal electrode plates. Because the metal electrodes would have little resistance in comparison to the buffer solution any potential applied to the electrodes would be uniformly distributed across their entire surface, thus providing a uniform electric field with which to elute the macromolecules from the slab gel. A platinum electrode is preferred because platinum is not readily degraded by electrolysis. The use of platinum foil for electrodes is impractical because of its high cost. Apparatus employing a stainless steel cathode plate with a platinum wire anode (Stellwag and Dahlberg, Nucleic Acid Research 8: 299–317 (1980), McLellan and Ramshaw, Biochemical Genetics 19: 647–654 (1981) and two graphite slabs weighing 3.75 lbs. each as anode and cathode, Gibson, Anal. Biochem. 118: 1–2 (1981) have been reported. However, operating units with these electrode designs require high current, e.g., 1.5A for two hours for the graphite slabs.

Bittner reports an apparatus employing 12 mil platinum wire for electrodes and cites indirect experimental evidence to conclude a homogeneous field is produced. The electrode is formed by stringing uninsulated platinum wire vertically 19 cm, horizontally 5.5 cm, again vertically for 19 cm, again horizontally for 5.5 cm and finally vertically for 19 cm. The distance of the two outer vertical portions of the platinum wire from the plexiglass walls of the apparatus are 2.4 cm. While it is not stated it appears from a diagram of the apparatus that the vertical portions of the wire forming the anode and cathode are aligned. The electrode assemblies are positioned very close (1.5 cm) to the gel. To infer that the electric field produced by this electrode design is uniform over the entire surface of the chromatographic gel, Bittner, et.al., compared the separation patterns of nucleic acids on 0.75% agarose gels with the separation pattern after transfer to the matrix and observed that the electroelution had occurred without distortion and with little loss of resolution. However, since nucleic acid transfers from agarose gels is readily accomplished by the technique of Southern blotting the validity of this test to conclude that a uniform electric field is generated by this electrode design is questionable. Even though the transferred patterns covered only 30% of the slab surface area they extrapolated their observation to the entire gel surface and concluded that the electrical field was uniform over the entire gel surface. Since electrode designs will produce uniform but different electric fields in different areas of a gel, the validity of extrapolating the observations from one area of a gel to the entire gel is questionable. Additionally, the fact that some loss of resolution does occur upon transfer further weakens inferences of a unifrom electric field.

The efficiency of the transfer of the individual macromolecular elements from the gel to the immobilizing matrix seems to depend on the chemical nature of the element, i.e., whether it is protein or nucleic acid, the composition of the gel and the molecular weight of the individual elements. Many researchers have reported that smaller molecular weight fragments from the electrophoretic separation of protein isolates on polyacrylamide gels are eluted with greater efficiency than larger fragments. See for example: Burnette, Anal. Biochem. 112: 195–203 (1981), Gershoni and Palade, Anal. Biochem. 124: 396–405 (1982), Howe and Hershey, J. Biol. Chem. 256 12836–12839 (1981), McLellan and Ramshaw, Biochem. Genet. 19: 647–654 (1981). This effect was documented particularly well by Howe and Hershey. By changing the immobilizing matrix every hour they were able to show that in two hours the low-molecular weight polypeptides were efficiently eluted whereas six hours were necessary to elute sufficient amounts of high molecular weight polypeptides. To illustrate contradiction in the state of the art, Bittner claims that proteins with a molecular weight range of 14,000 to 110,000 were eluted and transferred virtually quantitatively from a SDS polyacrylamide gel. Towbin, et.al., (Proc. Nat. Acad. Sci. U.S.A. 76, 4350–4354 (1979) reports quantitative transfers in urea but not in SDS polyacrylamide gels.

A number of suggestions have been made to overcome or mitigate this molecular weight bias in a transfer, among them (i) the use of reversible gel crosslinkers (Tas, et.al., Anal. Biochem. 100: 264–270 (1979) (instead of bisacrylamide), followed by gel depolymerization prior to transfer (Bolen, et.al., Appl. Environ. Microbiol. 43: 193-199 (1982), Renart, et.al., Proc. Nat. Acad. Sci. U.S.A. 76: 3116-3120 (1979)); (ii) limited protease digestion of high molecular weight proteins during electrophoretic transfer to convert them to smaller more easily elutable peptides (Gibson, Anal. Biochem. 118: 1-3 (1981)); (iii) addition of detergent SDS to "transfer buffer" to facilitate elution of high molecular weight proteins (Erickson, et.al., J. Immunol. Methods 51: 241-249 (1982). The effect of acrylamide concentration on protein elution has not been studied. One would expect that the elution of high molecular weight peptides would be affected by the porosity of the gel matrix (Gershoni and Palade, Anal. Biochem. 131: 1-15 (1983).

OBJECT AND SUMMARY OF THE INVENTION

To facilitate the description of the objects and the description of the invention, the following terms are described with respect to the longest sides (top to bottom) of the nonconductive box in which the electroblotting is performed:

(1) the frontal plane is the vertical plane which runs from top to bottom and left to right of the box;
(2) the saggital plane is the vertical plane which runs from top to bottom and front to back of the box; and
(3) the transverse plane is the horizontal plane which runs left to right and front to back of the box.

The samples to be separated by electrophoresis are placed at discreet positions at one end of the gel. The gel is placed in an electric field so that the samples migrate from the top to the bottom. Each sample defines a lane down which its components travel and are separated, after which the gel is placed in a second electric field, perpendicular to its surface, for the purpose of blotting.

It is an object of this invention to provide an improved method for producing uniform electric fields for blotting which is both economic and efficient i.e., requires minimal currents to electroelute the macromolecules from the chromatographic gels, e.g., polyacrylamide.

It is another object of this invention to provide a method for producing an electric field which is uniform at each transverse plane of the blotting apparatus but which varies in a controlled predetermined way along the frontal plane.

It is a further object of this invention to shorten the time required for the transfer of large molecular weight macromolecules relative to smaller molecular weight macromolecules from an chromatographic gel and to accomplish this without loss of the smaller molecular weight macromolecules.

It is a further object of this invention to improve the transfer of macromolecules from chromatographic gels so that quantitative assays in contrast to qualitative assays within a lane may be performed.

It is yet a further object of this invention to provide a means by which the intensity of the applied electric field may be measured and the gradient of the electric field be measured. It is of special importance in generating gradients to be able to monitor the applied field intensity.

An even further object of this invention is to provide the ability to continuously control the applied field intensity at each electrode pair, thus creating a vast combination of gradients. This object, coupled with the previous object, provides the user with a level of control and function previously unavailable.

Another object of this invention is to provide a tool by which the user is capable of measuring the relative field strength and its distribution within any apparatus. This provides the user with the ability to evaluate and monitor the fields generated by various electrode arrays.

These and other objects of the invention are achieved by using an electric field which is uniform over the entire length of a chromatographic gel or an electric field which varies in a predetermined and controlled way over the length of a chromatographic gel. The invention consists of multiple pairs of aligned electrodes of opposite charge, each pair accurately spaced from its adjacent pair of aligned electrodes. The end pairs of aligned electrodes must be accurately spaced from the nonconducting surfaces of the electroelution chamber.

Each aligned electrode pair is connected through a device capable of varying the applied electric potential. By varying the electric potential of each electrode pair the electric field along the length of the chromatographic gel can be uniformly varied. The chromatographic gel should be mounted midway between the aligned pairs of electrodes with equal but opposite charge. To monitor the applied electric potential, a voltmeter whose input can be switched to any selected electrode pair is used to measure the applied field intensity.

BRIEF DESCRIPTION OF THE DRAWINGS

The invention will be described with reference to the accompanying drawings, which form a part of this specification, and wherein.

DETAILED DESCRIPTION OF THE INVENTION

One parameter that directly affects the blotting process is the electric field which serves as the motive force that drives the elution of macromolecules. Variations in the electric field intensity cause variability in the elution process. Therefore, it is important to subject the macromolecules to the same field intensities to ensure their uniform transfer. Therefore, a reliable blotting apparatus should generate predictably uniform electric fields, i.e., fields without undesirable detectable changes in field intensity. The standard procedure employed to produce electric fields has been to use an array of platinum wire as the electrode. In practice, arrays of various configurations have been employed. The goal in routing the platinum wires comprising the electrode arrays of opposite charge was to use as little material as possible while at the same time attempting to route them so as to produce a uniform field. No direct measurements of the field intensities produced by the various configurations of electrode arrays have been reported. Aside from the qualitative evidence (cited in the Prior Art section) for the production of a uniform field with a particular electrode configuration the uniformity of the field produced over the surface of the gel by other electrode configurations is unknown.

To facilitate the design of an electrode array which would be efficient in the use of the electrode material but would also produce the desired uniform field at the frontal median plane a computer model was developed which permits the analyses of the electric fields of a very large number of simulated electrode arrays confined within a nonconductive box. Based upon these data an electrode array has been designed that generates either a highly uniform or a controlled gradient of field intensity. This capability to generate a gradient can provide an efficient solution to a major problem in macromolecule transfer that stems from the fact that elution efficiency of a macromolecule is related inversely to molecular weight. Since the gradient electric field can assume a variety of shapes the gradient can be tailored to experimental needs.

Figure 1:
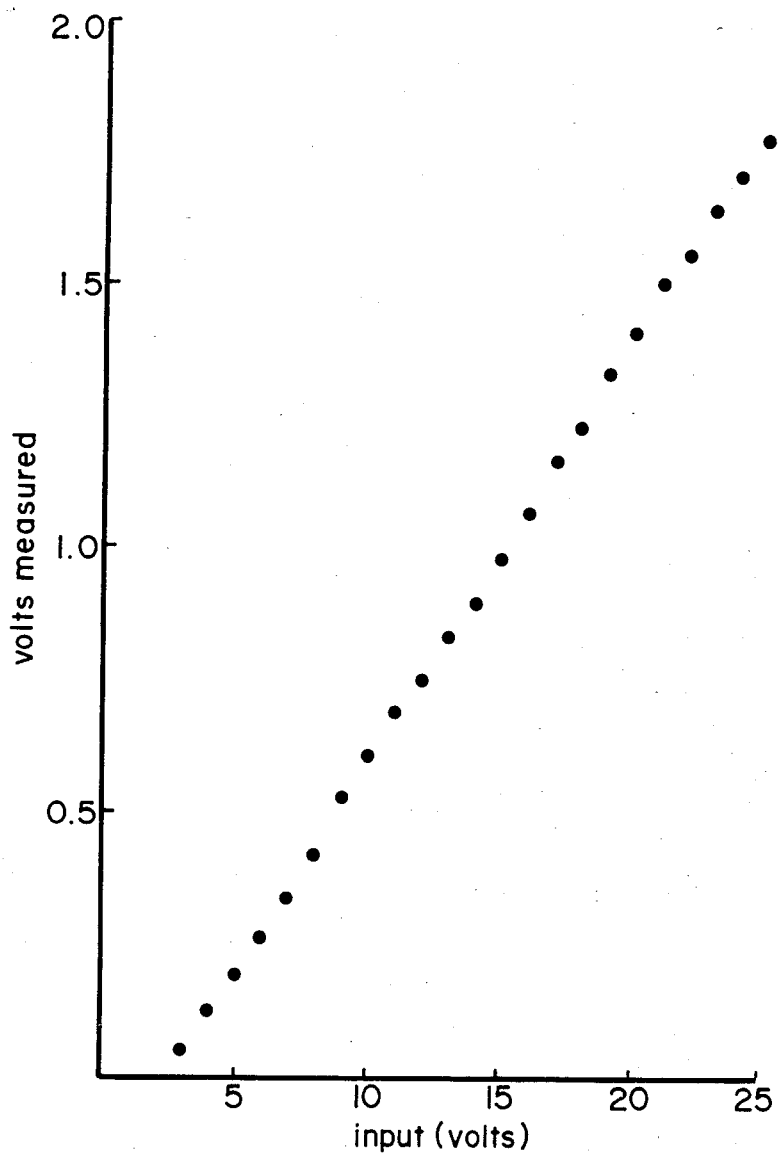
FIG. 1 is a plot showing the change in the electric field as a function of input voltage to the electrode array.

A device was constructed to allow the direct measurement of an electric field at various positions within the nonconductive box of a transfer apparatus. The device consists of a probe and a mounting mechanism that could be used to accurately position the probe vertically and horizontally. The probe consists of two square pieces (0.25 cm$^2$) of 15 mil platinum foil which are mounted parallel 1 cm. apart from each other each on the end of a calibrated plexiglass rod. The squares of platinum foil are connected via Teflon insulated wire to a voltmeter or other measuring device such as a computer. The mounting mechanism consists of a clamp which is mounted on a calibrated horizontal track and which holds the probe. The horizontal position of the probe can be determined manually or by a computer. The probe could be adjusted horizontally and vertically in a reproducible manner anywhere within the nonconductive box of the transfer apparatus. To test the efficacy of the device to measure the change in the electric field as a function of the input voltage to the electrode array, the series of measurements plotted in FIG. 1 were made. The plot demonstrates that the potential difference measured between the two squares of platinum foil was directly proportional to the electrical input to the transfer apparatus. The measured voltages are considered to reflect the average field intensity of the region of the nonconducting box in which the probe is suspended.

Each electrical measurement and each transfer recited in this application is conducted using 15.6 mM Tris, 120 mM glycine pH 8.3 as electrode buffer and a power supply which provides 200 mA constant current. Measurements are made while stirring the buffer thus reducing the effect of bubbles that otherwise accumulate around the electrode wires.

Figure 2:
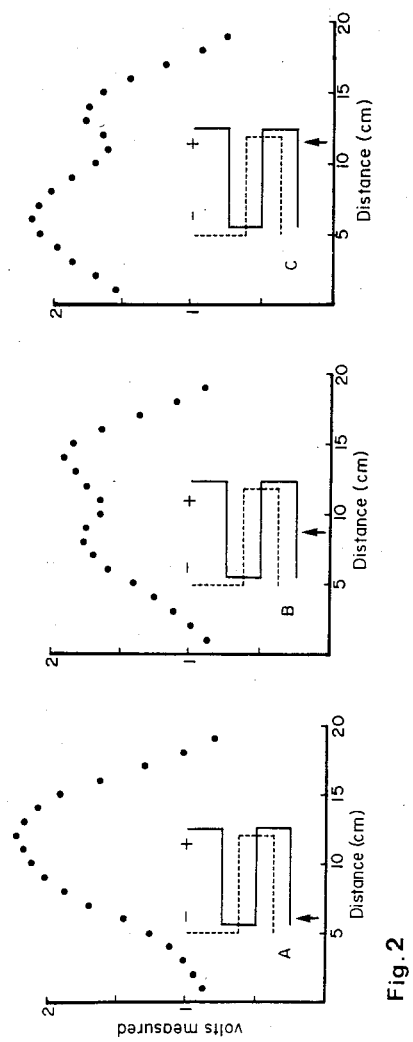
FIG. 2 is a graphical demonstration of the extensive variation in the electric field intensity measured in a commercially available apparatus.

To determine whether in fact uniform electric fields are produced, direct measurements of field intensities generated by a variety of transfer apparatus equipped with different configurations of electrode arrays (some commercially available) were made. These measurements clearly indicate that prior to this invention uniform electric fields were not produced at the surface of the gel. An actual demonstration of the extensive variation in the electric field intensity measured in a commercially available transfer apparatus which utilized an asymmetric electrode array design of three continuous horizontal lengths of platinum wire opposing two staggered horizontal lengths in which all the vertical cross connections are exposed is graphically reported in FIG. 2. FIG. 2 plots the volts measured (electric field) vs. the distance from the surface of the buffer toward the bottom of the box. The arrows in the accompanying electrode diagrams show the position of the probe for each scan. All scans of the field in the median frontal plane of the apparatus, run perpendicularly to the electrodes, show single or complex peaks in the center of the box and fall off unevenly at the top and bottom. Deviations in the field strength are quite prominent even when the median frontal plane is scanned parallel to the main lengths of this electrode array.

Figure 3:
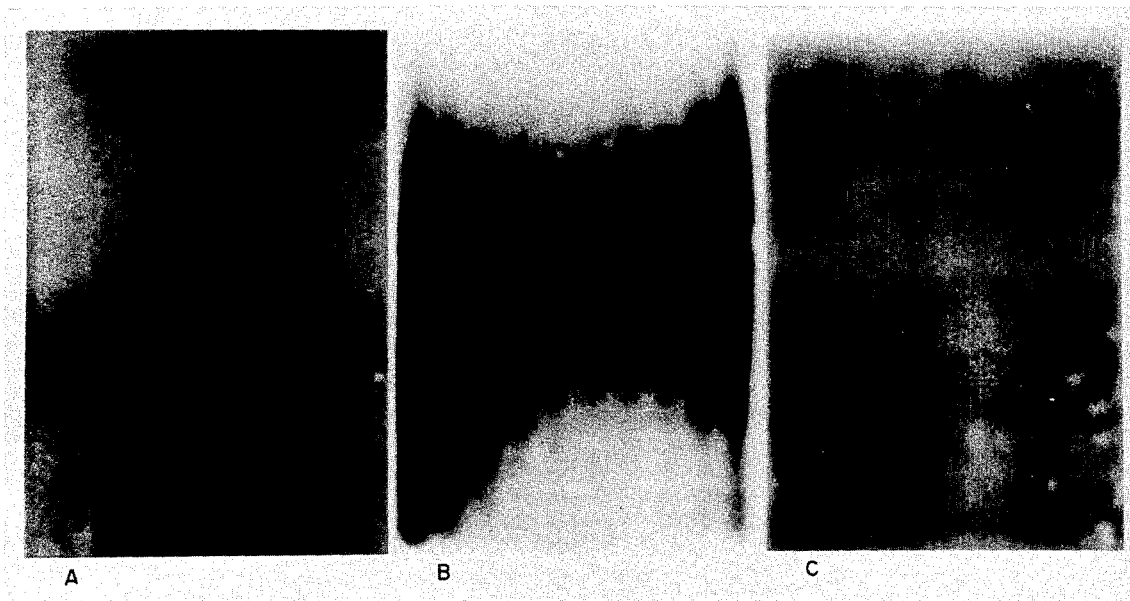
FIG. 3 shows autoradiograms of a series of transfers from gels containing uniform suspensions of a radioactive macromolecule.
Figure 4:
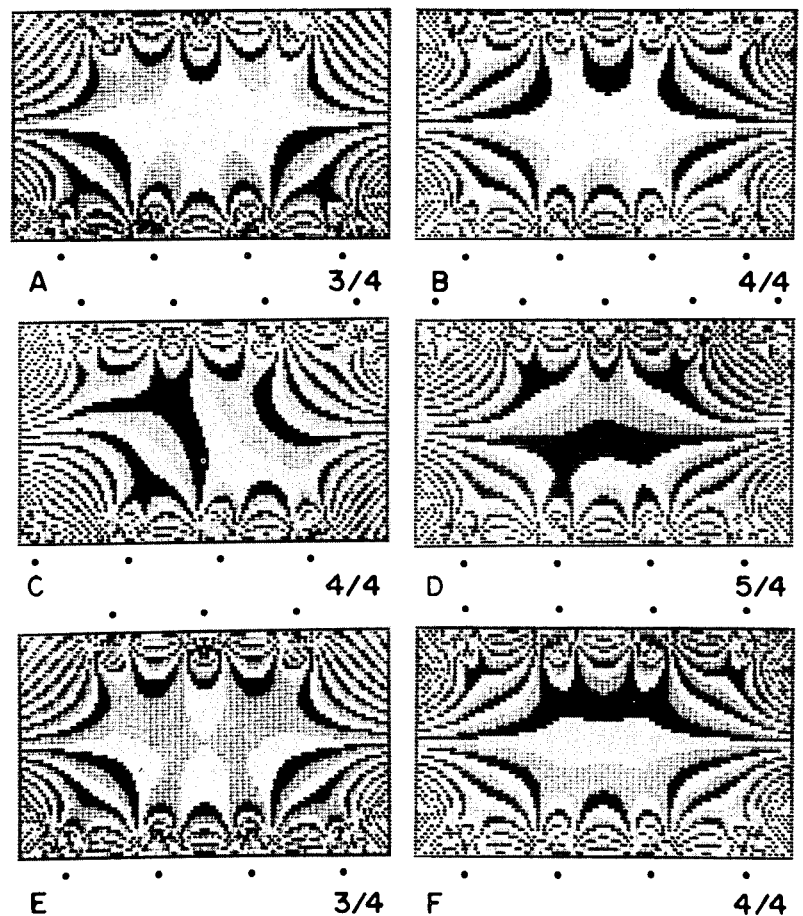
FIG. 4 shows computer simulations of asymmetric electrode arrays.

To prove that nonuniform electric fields do adversely affect both qualitatively and quantitatively the transfer of macromolecules from chromatographic gels, a series of transfers from gels containing a uniform suspension of a radioactive macromolecule were performed (FIG. 3). These polyacrylamide gels containing uniform suspensions of radioactive protein were prepared by solubilizing 1-2 $\mu$Ci$^{125}$I-labeled bovine serum albumin in 0.9 ml of 10% aqueous SDS. This preparation was added to 89.1 ml of a 10% acrylamide in Tris-HCl buffer pH 8.8 and the resulting mixture was polymerized to yield a 10% polyacrylamide gel containing 0.1% SDS and a uniform suspension of radioactive protein. This is demonstrated by the autoradiogram of such a gel in FIG. 3A. These gels were then used for transfer to membrane filters. The autoradiograms of such filters demonstrate the topography of the electric field generated in the particular transfer apparatus being tested. A uniform electric field produces uniformly exposed autoradiograms (FIG. 3C) whereas autoradiograms produced from transfers conducted with nonuniform electric fields will produce autoradiograms with varying degrees of exposure. FIG. 3B is the autoradiograms of the blot obtained by transferring such a gel in the apparatus analyzed in FIG. 2. The variations measured are reflected as differential efficiency in transfer of $^{125}$I-labeled bovine serum albumin. That such peaking in the center of the frontal plane appears to be a characteristic trait to asymmetric arrays in general is demonstrated in the computer simulations (FIG. 4).

Computer simulation of the electric fields generated by different designs of electrode arrays is based on the mathematical expression which is derived from basic principles of electrostatics. A computer model was generated by defining the boundaries of a non-conductive box and the locations and the coordinates of electrode elements within it. The computer scans over a selected plane within the confines of the box and calculates the potential generated by the electrode elements at each point on the plane. This value is then quantized into 0.2 volt intervals. The levels are then plotted onto the display at the specified coordinates. To facilitate visual observation, the output is transposed into three grey scale values and printed. The potential change from one grey scale value to the next is 0.2 volts.

For each simulation the box dimensions and electrical input have been kept constant. FIG. 4A-F depict the topography of the electric field in the median transverse plane generated by pairs of electrodes within a box where the anode consists of four vertical lengths and the cathode of three, four, or five lengths as indicated. The positions of the electrode elements can be determined from the reference points designated beyond the walls of the box. The median of the plane is the plane where uniform electric fields would be expected. Note that the four elements of the cathode and the anode in FIG. 4C are staggered and compare this array to the directly aligned elements as in the case for FIG. 4B. The increase in nonuniformity with nonalignment is dramatic. The contribution to the field from the connecting wires between the elements has been accounted for in FIG. 4A–D. FIG. 4E–F depict the same electrode configuration as FIG. 4A–B respectively, however, the connecting wires are insulated and do not affect the electric field. It is apparent from FIG. 4 that the most promising electrode configuration is the symmetrical 4×4 array. Further fine tuning of this array is accomplished by placing the outer electrode elements in a plane deeper into the box bringing them closer to each other, thereby increasing the field directly between them. This has the effect of broadening as well as extending considerably the region of uniformity into other medial frontal planes.

Figure 5:
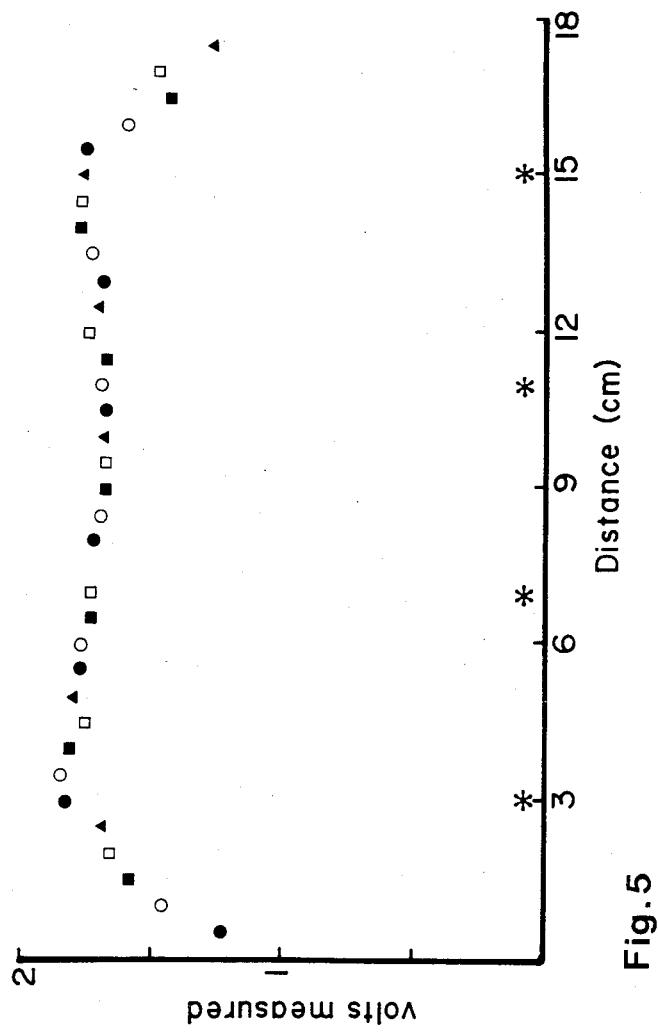
FIG. 5 shows the measured electric field in the transfer box of the instant invention.
Figure 6:
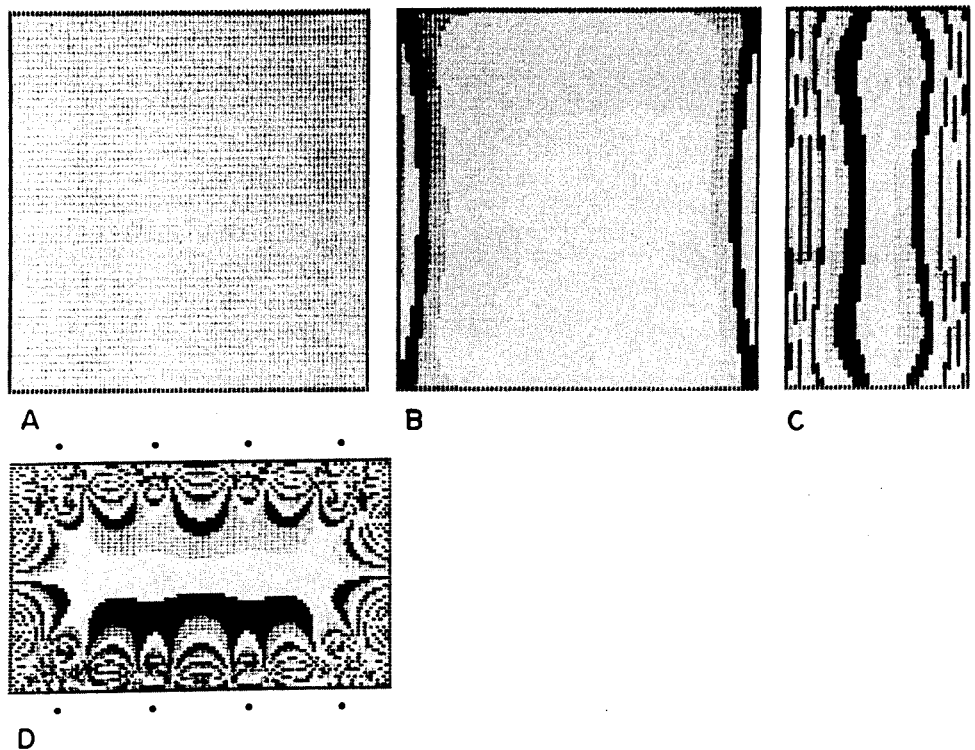
FIG. 6 presents computer generated models of the transfer box of the instant invention.

Utilizing the results from the computer simulation of the electric field from various configurations of electrode arrays, a transfer box equipped with the symmetrical 4×4 configuration of an electrode array was constructed and tested. The nonconductive box measures 10×16×24 cms. Four vertical lengths of a continuous platinum wire opposed directly a second array of four vertical lengths identical to the first, the electrodes in each pair being placed the same distance from the sides of the box. The length of each vertical wire was 20.5 cm. gel. The diameter of the wire was 14 mil. The two outer most lengths of each electrode wire were positioned 0.3 cm closer to the median frontal plane of the box than were the other two lengths which were directly against the surface of the wall. The distance between each of the four vertical lengths was 4 cms. All the cross connecting wires were insulated and thus did not contribute to the electric field. The distance between the anode and the cathode was 7.5 cm. FIG. 5 shows the measured electric field in this transfer box. The field was measured across the frontal median plane at 5 depths (every 4 cm; each depth is designated by a different symbol) from the buffer surface. The plot demonstrates the uniformity of the field. Computer generated "field maps" of such a box are presented in FIG. 6. (A is the frontal median plane, B is 0.5 cm off the median plane, C is the median saggital plane, and D is the median transverse plane). The uniformly darkened autoradiogram shown in FIG. 3C demonstrates that this apparatus gives a uniform transfer of $^{125}I$-labeled bovine serum albumin. This configuration of electrode wires ensures that a uniform electric field can be reliably and reproducably generated. This ensures that quantitative transfers of macromolecules of the same molecular weight in every lane in a chromatographic gel will occur.

Measurements of the electric fields generated by the electrode array of the same configuration but with insulated or uninsulated connecting wires indicates clearly that wider, more symmetrical and more uniform fields are obtained in the frontal central region of the box when the connecting wires are insulated. Therefore, in the most preferred embodiment, these connecting wires are omitted altogether. The electrode array consists of an equal number of independent, aligned wire lengths, equally spaced from one another mounted to the walls of the box. Whether the aligned wires are to be mounted horizontally or vertically depends on the orientation of the chromatographic gel. The spacing between the aligned independent wires depends on the number of aligned wire pairs and the dimensions of the box. In the most preferred embodiment the box is the same dimensions as previously described. In the most preferred embodiment 5 independent pairs of aligned electrodes are employed. The aligned pairs are equispaced from each other and from the side walls of the box. When all five pairs of electrodes are connected directly to the power supply they function as would be expected of a continuous wire electrode with 5 horizontal lengths and insulated connecting wires.

In addition to providing highly homogeneous fields this electrode arrangment offers the possibility of generating controlled variable fields of which linear gradient fields are of particular interest. Field gradients may be generated in a variety of ways both mechanical and electrical. Some mechanical means include tilting the electrode array such that one end, for example the bottom end, has a closer distance from anode to cathode than the other end. The bottom end would therefore have a higher field intensity although it would be more difficult to adjust reproducibly. Another mechanical means would employ a mask to be sandwiched between the chromotographic gel-membrane filter assembly and an electrode. The characteristics of this mask would be to have a variable degree of electrical impedance from one end to the other. Such a characteristic could be obtained either through the manipulation of the mask composition or by varying the porosity of the material from one end to the other. The net result of the mask placed in a homogeneous field would be to generate a controlled gradient over the surface of the gel. Such masks would be expensive to manufacture and separate masks would be necessary to create different gradient fields. Yet another mechanical means of producing a gradient would be a system to physically remove the chromatographic gel-membrane filter assembly from the buffer with the electric field at a controlled rate. The net effect of such a system would be to cause a variable exposure time to the electric field. Thus the chromatographic gel first removed at the top would receive the least exposure while the bottom of the chromatographic gel would receive the applied field for the full time duration. Though this system would work, it is laden with problems, not the least of which is the drying of the gel once it is removed from the buffer.

One electrical means of producing a gradient field would be to provide independent power sources for each electrode pair. Such a system would provide an easy means to manipulate the gradient but would be prohibitively expensive to become practical. Another electrical means would be to use a single power source but a system of independent voltage or current regulators for each electrode pair. This would maintain the ease of adjustment of the former method and would be less expensive. A simpler method still is to provide either fixed resistors in series with each electrode pair which could then be switched to establish different gradients or a set of variable resistors for each electrode pair so that the field could be continuously varied. The method employed in the most preferred embodiment of the invention uses a combination of the above methods a switch selects fixed resistors for preset gradients as well as potentiometers for continuously variable gradients.

Whether setting variable gradients with potentiometers or observing the effects of chromatographic gels in uniform fields, it is extremely useful to monitor the applied potentials at each electrode pair. This capability is realized in the preferred embodiment of this invention through the use of a voltmeter, either housed within the control box or attached externally, whose input can be switched to any selected electrode pair in order to measure the applied field intensity. It is connected through the selecting switch directly to the opposing pairs of electrodes after the series resistance to the power supply.

Figure 7:
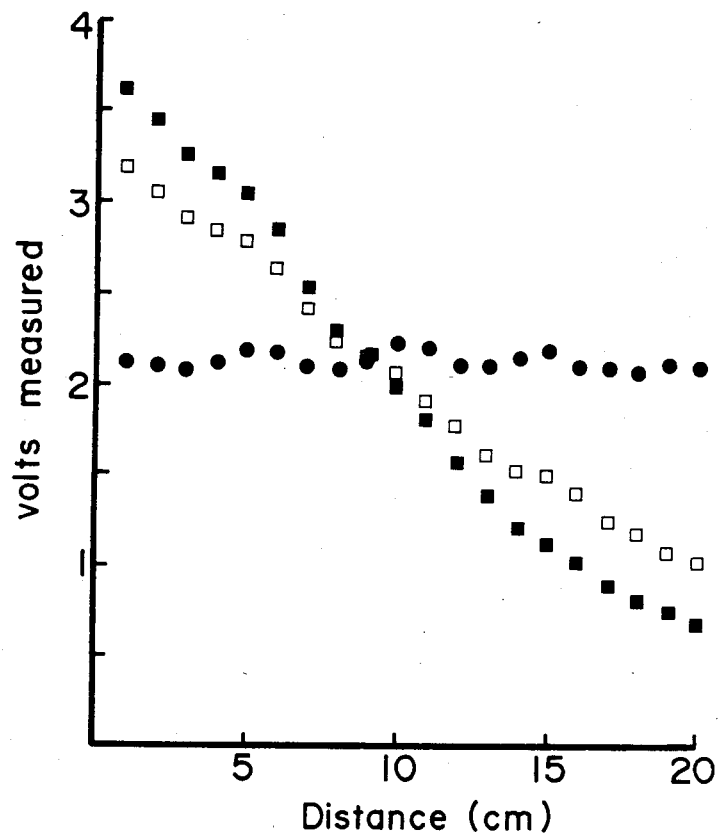
FIG. 7 is an illustration of the utility of five independent, aligned electrode pairs to produce both a very uniform field and gradient fields.

FIG. 7 is a plot of the electric field measured from top to bottom at the frontal median plane. FIG. 7 illustrates the utility of the five independent, aligned electrode pairs to produce both a very uniform field (solid dots) and gradient fields (solid squares, 65 V–15 V; open squares, 40 V–20 V).

To demonstrate the effect of the molecular weight of a macromolecule on its transfer from a gel, $^{125}$I-labeled proteins of different molecular weight were used as standards. These standards were separated on SDS/5-15% polyacrylamide gradient gels and then blotted to nitrocellulose membrane filters.

Figure 8:
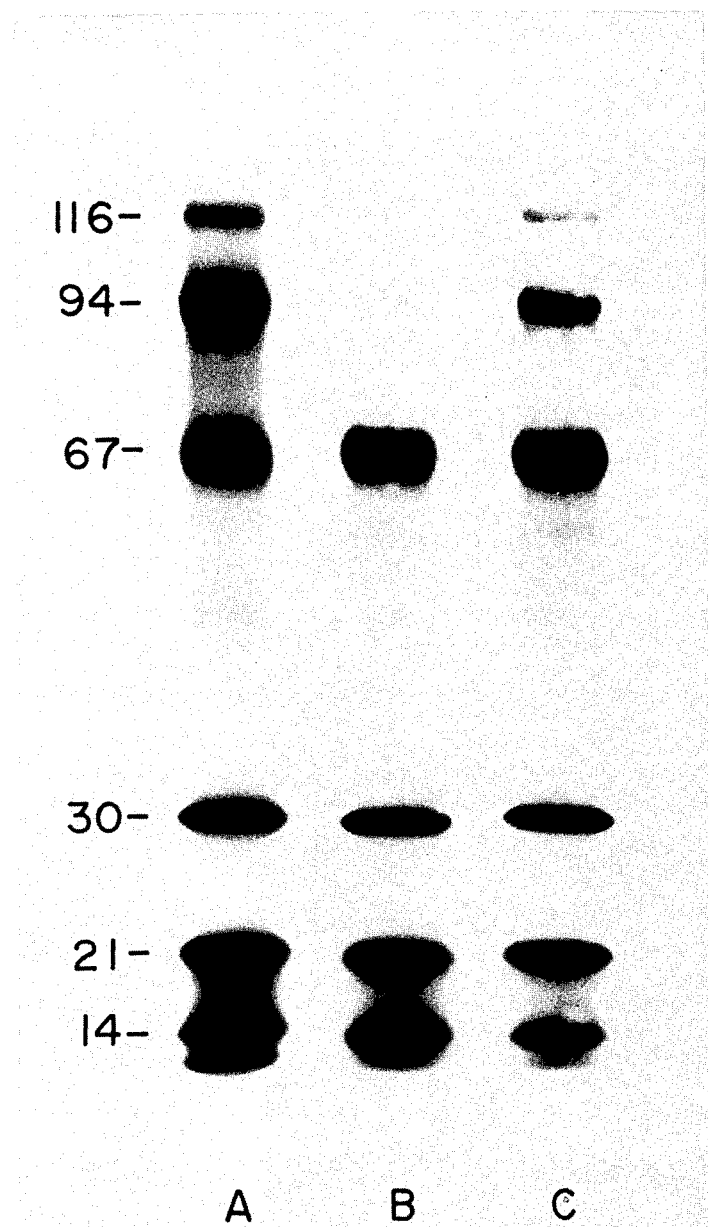
FIG. 8 is a demonstration of the utility of gradient field blotting.

FIG. 8 clearly demonstrates the utility of gradient field blotting. As noted above, the speed of electroelution of macromolecules at constant current is inversely proportional to their molecular weight (the numbers in FIG. 8 designate molecular mass in kilodaltons). If the voltage, current and time conditions are selected so as to optimize the electroelution of the lower molecular weight macromolecules, the larger molecular weight components are retained by the gel. If the voltage, current and time conditions are optimized to elute the high molecular weight components, the lower molecular weight components are eluted so rapidly that they cannot be retained by the immobilizing matrix. FIG. 8 compares gradient field electroelution (C) with the conventional method of uniform field (25 volts, B) electroelution (A, is an autoradiogram of a sample gel prior to transfer). It is apparent in the uniform field transfer that high molecular weight components are dramatically diminished in quantity. This is in contrast to the linear gradient field (15–65 volts) in which a more uniform and therefore a more quantitative transfer of all of the components from the gel is obtained (compare A to C). Therefore, gradient fields provide two very significant advantages. First, there exists the possibility of preferentially accelerating the high molecular weight proteins while slowly eluting the low molecular weight proteins. Slow transfer of the smaller proteins is found to be advantageous as it gives the macromolecules more time interact with the matrix material thus limiting the extent to which they are blown through the filter. Secondly, the gradient allows better use of common power supplies. By redistributing the field strength, high potential differences, e.g., 65 V, can be generated where needed and sufficiently low, e.g., 15 V, provided at the lower end of the gradient while still running the system with modest currents, e.g. 200 mA.

We claim:

1. An improved method of electroblotting macromolecules from a chromatographic gel to an immobilizing matrix wherein the improvement comprises:
   (a) measuring the electric field produced by two or more sets of electrodes, each set of electrodes comprising an anode and a cathode which are located in the same saggital plane within the container, whose electric potential can be varied and adjusted independent from other said sets of electrodes and which said sets of electrodes are equispaced from other said sets of electrodes; and (b) exposing a chromatographic gel and immobilizing matrix placed in a non-conductive container containing a buffer to the measured electrical field.

2. An improved method as in claim 1 wherein the electric potential of each said set of electrodes is varied to produce an electric field as measured at the gel-matrix interface.

3. An improved method as in claim 1 wherein the electric potential of each said set of electrodes is varied to produce the same electric field at the gel-matrix interface.

4. An improved method as in claim 1 wherein the electric potential of each said set of electrodes is varied to produce an electric field which increases linearly along the gel-matrix interface.

* * * * *